United States Patent
Hall et al.

(10) Patent No.: US 12,057,037 B2
(45) Date of Patent: Aug. 6, 2024

(54) USER INTERFACE SYSTEMS FOR STERILE FIELDS AND OTHER WORKING ENVIRONMENTS

(71) Applicant: Medos International Sarl, Le Locle (CH)

(72) Inventors: Mark Hall, Bridgewater, MA (US); Roman Lomeli, Plymouth, MA (US); J. Riley Hawkins, Cumberland, RI (US); Joern Richter, Kandern (DE)

(73) Assignee: Medos International Sarl, Le Locle (CH)

( * ) Notice: Subject to any disclaimer, the term of this patent is extended or adjusted under 35 U.S.C. 154(b) by 397 days.

(21) Appl. No.: 17/321,390

(22) Filed: May 14, 2021

(65) Prior Publication Data

US 2021/0272487 A1    Sep. 2, 2021

Related U.S. Application Data

(63) Continuation of application No. 16/782,035, filed on Feb. 4, 2020, now Pat. No. 11,024,207, which is a
(Continued)

(51) Int. Cl.
*G09G 3/00*     (2006.01)
*A61B 1/04*     (2006.01)
(Continued)

(52) U.S. Cl.
CPC .............. *G09G 3/002* (2013.01); *A61B 1/042* (2013.01); *A61B 17/00* (2013.01); *A61B 34/25* (2016.02);
(Continued)

(58) Field of Classification Search
CPC .............................. G06F 3/017; G06T 19/006
See application file for complete search history.

(56) References Cited

U.S. PATENT DOCUMENTS

| | | |
|---|---|---|
| 5,543,832 A | 8/1996 | Oravecz et al. |
| 5,788,688 A | 8/1998 | Bauer et al. |

(Continued)

FOREIGN PATENT DOCUMENTS

| | | |
|---|---|---|
| CN | 105518575 A | 4/2016 |
| DE | 10 2010 027526 A1 | 1/2012 |

(Continued)

OTHER PUBLICATIONS

Cheok et al., "Magic Land—A mixed reality interactive system integrating 3D live persons", Mixed Reality Laboratory Singapore, 2004.

(Continued)

*Primary Examiner* — Shivang I Patel
(74) *Attorney, Agent, or Firm* — Barnes & Thornburg LLP

(57) ABSTRACT

User interface systems for sterile fields and other working environments are disclosed herein. In some embodiments, a user interface system can include a projector that projects a graphical user interface onto a data board or other substrate disposed within a working environment. The system can also include a camera or other sensor that detects user interaction with the data board or substrate. Detected user interactions can be processed or interpreted by a controller that interfaces with equipment disposed outside of the working environment, thereby allowing user interaction with such equipment from within the working environment. The data board can be an inexpensive, disposable, single-use component of the system that can be easily sterilized or another component suitably prepared for use in a sterile field.

16 Claims, 6 Drawing Sheets

Related U.S. Application Data continuation of application No. 16/001,182, filed on Jun. 6, 2018, now Pat. No. 10,593,240.

(60) Provisional application No. 62/516,897, filed on Jun. 8, 2017.

(51) Int. Cl.

| | | |
|---|---|---|
| *A61B 17/00* | (2006.01) | |
| *A61B 34/00* | (2016.01) | |
| *A61B 34/20* | (2016.01) | |
| *A61B 90/00* | (2016.01) | |
| *A61B 90/96* | (2016.01) | |
| *A61B 90/98* | (2016.01) | |
| *G06F 3/01* | (2006.01) | |
| *G06F 3/04842* | (2022.01) | |
| *G06F 3/04845* | (2022.01) | |

(52) U.S. Cl.
CPC ............ *A61B 90/36* (2016.02); *A61B 90/361* (2016.02); *G06F 3/017* (2013.01); *G06F 3/04842* (2013.01); *G06F 3/04845* (2013.01); *A61B 2017/00207* (2013.01); *A61B 2017/00216* (2013.01); *A61B 2034/2048* (2016.02); *A61B 2034/2057* (2016.02); *A61B 2034/2065* (2016.02); *A61B 2090/365* (2016.02); *A61B 2090/366* (2016.02); *A61B 2090/368* (2016.02); *A61B 2090/372* (2016.02); *A61B 2090/376* (2016.02); *A61B 2090/3966* (2016.02); *A61B 90/96* (2016.02); *A61B 90/98* (2016.02)

(56) References Cited

U.S. PATENT DOCUMENTS

| | | |
|---|---|---|
| 5,792,147 A | 8/1998 | Evans et al. |
| 6,020,917 A | 2/2000 | Oravecz et al. |
| 6,175,610 B1 | 1/2001 | Peter |
| 6,307,674 B1 | 10/2001 | Sauer et al. |
| 6,857,746 B2 | 2/2005 | Dyner |
| 7,317,954 B2 | 1/2008 | McGreevy |
| 7,317,955 B2 | 1/2008 | McGreevy |
| 7,519,223 B2 | 4/2009 | Dehlin et al. |
| 8,682,030 B2 | 3/2014 | Large |
| 8,996,173 B2 | 3/2015 | Itkowitz et al. |
| 9,041,691 B1 | 5/2015 | Haskin et al. |
| 9,129,054 B2 | 9/2015 | Nawana et al. |
| 9,196,067 B1 | 11/2015 | Freed et al. |
| 9,542,001 B2 | 1/2017 | Birkenbach et al. |
| 10,593,240 B2 | 3/2020 | Hall et al. |
| 11,024,207 B2 | 6/2021 | Hall et al. |
| 2002/0077533 A1 | 6/2002 | Bieger et al. |
| 2005/0128184 A1 | 6/2005 | McGreevy |
| 2005/0195587 A1 | 9/2005 | Moctezuma De La Barrera et al. |
| 2006/0079752 A1 | 4/2006 | Anderl et al. |
| 2006/0176242 A1 | 8/2006 | Jaramaz et al. |
| 2007/0016008 A1 | 1/2007 | Schoenefeld |
| 2008/0125218 A1 | 5/2008 | Collins |
| 2011/0288964 A1 | 11/2011 | Linder et al. |
| 2012/0078088 A1 | 3/2012 | Whitestone et al. |
| 2012/0229383 A1 | 9/2012 | Hamilton et al. |
| 2013/0093788 A1 | 4/2013 | Liu et al. |
| 2013/0218024 A1 | 8/2013 | Boctor et al. |
| 2013/0249786 A1 | 9/2013 | Wang |
| 2014/0022283 A1 | 1/2014 | Chan et al. |
| 2014/0088990 A1* | 3/2014 | Nawana ................. G16H 50/20 705/2 |
| 2014/0201666 A1 | 7/2014 | Bedikian et al. |
| 2015/0209114 A1 | 7/2015 | Burkholz et al. |
| 2015/0268773 A1 | 9/2015 | Sanaullah et al. |
| 2016/0022374 A1* | 1/2016 | Haider ................. A61B 17/142 606/96 |
| 2016/0132122 A1 | 5/2016 | Steinle et al. |
| 2016/0180046 A1 | 6/2016 | Sezeur et al. |
| 2016/0331460 A1* | 11/2016 | Cheatham, III ...... A61B 5/7405 |
| 2016/0331461 A1 | 11/2016 | Cheatham, III et al. |
| 2016/0334864 A1 | 11/2016 | Cheatham, III et al. |
| 2016/0378938 A1 | 12/2016 | Kuhrt et al. |
| 2016/0378939 A1 | 12/2016 | Baumberger et al. |
| 2017/0042631 A1 | 2/2017 | Doo et al. |
| 2018/0286132 A1 | 10/2018 | Cvetko et al. |
| 2019/0012944 A1 | 1/2019 | Hall et al. |
| 2020/0251028 A1 | 8/2020 | Hall et al. |

FOREIGN PATENT DOCUMENTS

| | | |
|---|---|---|
| JP | 2014132980 A | 7/2014 |
| WO | 2015164402 A1 | 10/2015 |
| WO | 2016023123 A1 | 2/2016 |
| WO | 2017089910 A1 | 6/2017 |

OTHER PUBLICATIONS

International Search Report and Written Opinion issued Oct. 10, 2018, for Application No. PCT/US2018/036284 (15 pages).

Lee, J. C., Human Computer Interaction Institute, Carnegie Mellon University, YouTube video, published Dec. 21, 2007 <https://www.youtube.com/watch?v=Jd3-eiid-Uw>.

Vincent, J, "Sony's crazy projector that turns any surface into a touchscreen is going on sale this year,", Feb. 27, 2017, (web article) <https://www.theverge.com/circuitbreaker/2017/2/27/14737824/sony-xperia-touch-projector-android-touchscreen-mwc-2017.

Jesus Caban, "Information Technology for Next-Generation of Surgical Environments", 2006, University of Kentucky Master's Theses.

Office Action for Chinese Application No. 201880037819.1, dated Sep. 28, 2022 (16 pages).

Office Action for Japanese Application No. 2019-567714, dated Oct. 11, 2022 (6 pages).

U.S. Appl. No. 16/001,182, filed Jun. 6, 2018, User Interface Systems for Sterile Fields and Other Working Environments.

U.S. Appl. No. 16/782,035, filed Feb. 4, 2020, User Interface Systems for Sterile Fields and Other Working Environments.

Office Action for European Application No. EP 18738036.5 dated Sep. 20, 2023 (3 pages).

\* cited by examiner

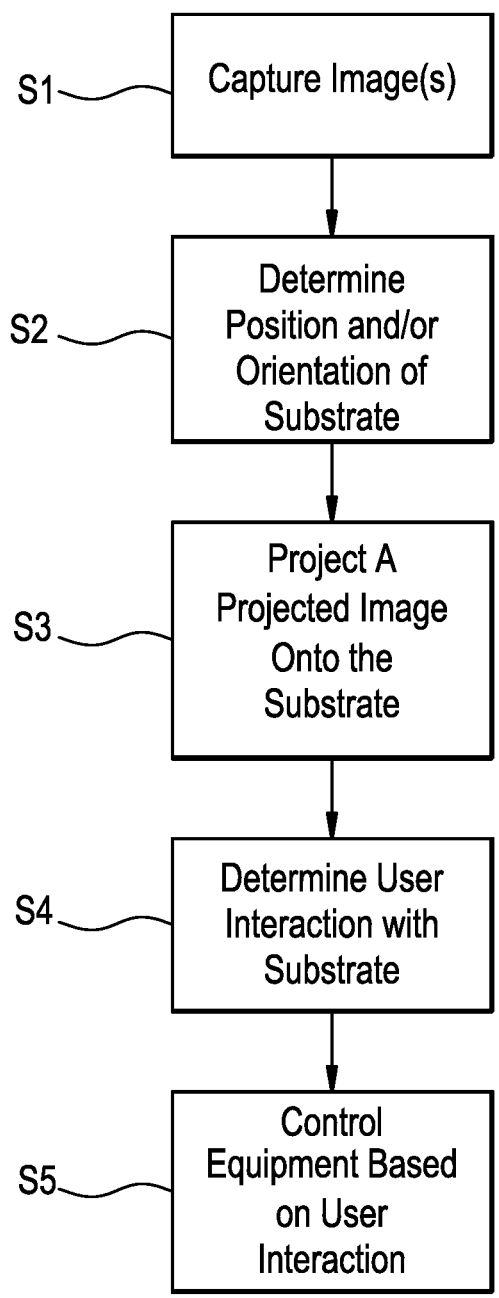

USER INTERFACE SYSTEMS FOR STERILE FIELDS AND OTHER WORKING ENVIRONMENTS

CROSS-REFERENCE TO RELATED APPLICATIONS

This application is a continuation of U.S. application Ser. No. 16/782,035, filed on Feb. 4, 2020. U.S. application Ser. No. 16/782,035 is a continuation of U.S. application Ser. No. 16/001,182 (now issued as U.S. Pat. No. 10,593,240). U.S. application Ser. No. 16/001,182 claims the benefit of U.S. Provisional Application No. 62/516,897, filed on Jun. 8, 2017. The entire contents of each of these applications are incorporated by reference herein.

FIELD

User interface systems for sterile fields and other working environments are disclosed herein, e.g., for allowing interaction with equipment disposed outside of the working environment from within the working environment.

BACKGROUND

Computer systems, mobile devices, electronics, and other equipment have become a common part of our everyday lives and use of such equipment has become a valuable tool in many medical, commercial, and industrial processes. Use of such equipment can be challenging in certain working environments.

In a surgical operating room, for example, it can be important to maintain a sterile field to reduce the risk of patient infection or other complications. Any equipment that is to be used in the surgery must be sterilized before being brought into the sterile field, or must remain outside of the sterile field. Some equipment, such as electronic devices, can be prohibitively difficult, expensive, or time-consuming to sterilize. These issues can be avoided by keeping the equipment outside of the sterile field, however doing so makes it challenging for those within the sterile field to interact with the equipment.

For example, a surgeon in the sterile field cannot simply reach out and turn a knob, press a button, or touch a touchscreen of a non-sterile piece of equipment. Rather, the surgeon must typically provide verbal instructions or gesture to an equipment operator outside of the sterile field, who then performs the equipment interaction desired by the surgeon. This exchange can be distracting for the surgeon, who must momentarily turn their attention away from the task at hand. It can also be frustrating for all involved, for example if the equipment operator is not as adept at using the equipment as the surgeon is, or if the equipment operator misunderstands the surgeon's request. In some instances, the surgeon leaves the sterile field in order to interact with a non-sterile piece of equipment. The surgeon must then go through the cumbersome procedure of re-sterilizing hands, gloves, clothing, etc., before reentering the sterile field. Even when proper procedures are followed, leaving and reentering the sterile field can increase the risk of contamination. Exemplary equipment that is typically disposed outside of the sterile field and with which the surgeon may wish to interact can include surgical navigation systems, PACS (picture archiving and communication systems), cameras, electrosurgical generators, infusion pumps, vacuum valves, music players, and the like.

Even equipment with which non-contact use is possible, such as an electronic display screen, can be inconvenient to use from within the sterile field. For example, the surgeon may need to turn their head to an uncomfortable position, or look away from the patient or the surgeon's hands, in order to view the display screen.

While a surgical operating room environment is described above, it will be appreciated that these challenges can be present in many other working environments, such as decontamination rooms, wet environments, clean rooms, areas with high humidity, dust, vibration, radiation, chemicals, temperature extremes, pressure, electromagnetic interference (EMI), electrostatic discharge (ESD), and/or other harsh environments.

In view of these and other challenges, there is a need for improved user interface systems for sterile fields and other working environments.

SUMMARY

User interface systems for sterile fields and other working environments are disclosed herein. In some embodiments, a user interface system can include a projector that projects a graphical user interface onto a data board or other substrate disposed within a working environment. The system can also include a camera or other sensor that detects user interaction with the data board or substrate. Detected user interactions can be processed or interpreted by a controller that interfaces with equipment disposed outside of the working environment, thereby allowing user interaction with such equipment from within the working environment. The data board can be an inexpensive, disposable, single-use component of the system that can be easily sterilized. The data board can be free of electronics or other components that may be sensitive to conditions within the working environment, or to procedures (e.g., sterilization) required to prepare the data board to enter the working environment (e.g., a sterile field). In other embodiments, however, the data board can include electronic components (e.g., e-paper screens, liquid crystal screens, tablet computers, etc.) suitably prepared for use in a sterile field.

In some embodiments, a user interface system can include a camera configured to capture images of a working environment in which a substrate is disposed; a controller that determines, from the captured images, a position and orientation of the substrate within the working environment and changes in said position and orientation; and a projector that projects a projected image onto the substrate, the projected image or the location of the projected image being adjusted by the controller in response to changes in the determined position or orientation of the substrate; wherein the controller further determines, from the captured images, whether and how a user is interacting with the substrate.

The working environment can include a sterile field in a surgical operating room. The substrate can include a data board. The data board can include a unique identifier. The data board can include a position marker. The data board can include static, non-projected user interface elements. In some embodiments, the data board does not include electronics. The substrate can include a skin surface of a patient, a glove, or a sterile dressing. The substrate can include a surgical instrument. The projected image can include an indicator as to whether the surgical instrument is disposed along a predetermined trajectory. The projected image can include an indicator as to whether the surgical instrument or a portion thereof, or an implant connected thereto, is adjacent to or within a delineated proximity to a predetermined surgical site. The projected image can include a graphical user interface. The projected image can include a camera feed from a camera inserted into a patient through an access device. The projected image can include display of information, including warnings or error messages in some embodiments. The projected image can include a display of, or information received from, a piece of controlled equipment. The controller, responsive to user interaction with the graphical user interface, can control equipment disposed outside of the working environment. The controller, responsive to user interaction with the graphical user interface, can control equipment disposed within the working environment.

In some embodiments, a user interface method can include capturing one or more images of a working environment in which a substrate is disposed; determining, with a controller, a position and orientation of the substrate from said one or more captured images; projecting a projected image onto the substrate based on the detected position and orientation; and determining, with the controller, whether and how a user interacts with the substrate based on said one or more captured images.

The method can include, with the controller, controlling equipment disposed outside of the working environment based on user interaction with the substrate as determined by the controller. The method can include, with the controller, controlling equipment disposed within the working environment based on user interaction with the substrate as determined by the controller. The method can include detecting changes in the position or orientation of the substrate and adjusting the position or orientation of the projected image accordingly. The user interaction can include a hand gesture or use of a stylus.

BRIEF DESCRIPTION OF THE DRAWINGS

FIG. 5 is a flow chart of an exemplary method of using the system of FIG. 1;

DETAILED DESCRIPTION

User interface systems for sterile fields and other working environments are disclosed herein. In some embodiments, a user interface system can include a projector that projects a graphical user interface onto a data board or other substrate disposed within a working environment. The system can also include a camera or other sensor that detects user interaction with the data board or substrate. Detected user interactions can be processed or interpreted by a controller that interfaces with equipment disposed outside of the working environment, thereby allowing user interaction with such equipment from within the working environment. The data board can be an inexpensive, disposable, single-use component of the system that can be easily sterilized. The data board can be free of electronics or other components that may be sensitive to conditions within the working environment, or to procedures (e.g., sterilization) required to prepare the data board to enter the working environment (e.g., a sterile field). In other embodiments, however, the data board can include electronic components (e.g., e-paper screens, liquid crystal screens, tablet computers, etc.) suitably prepared for use in a sterile field.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Figure 1:
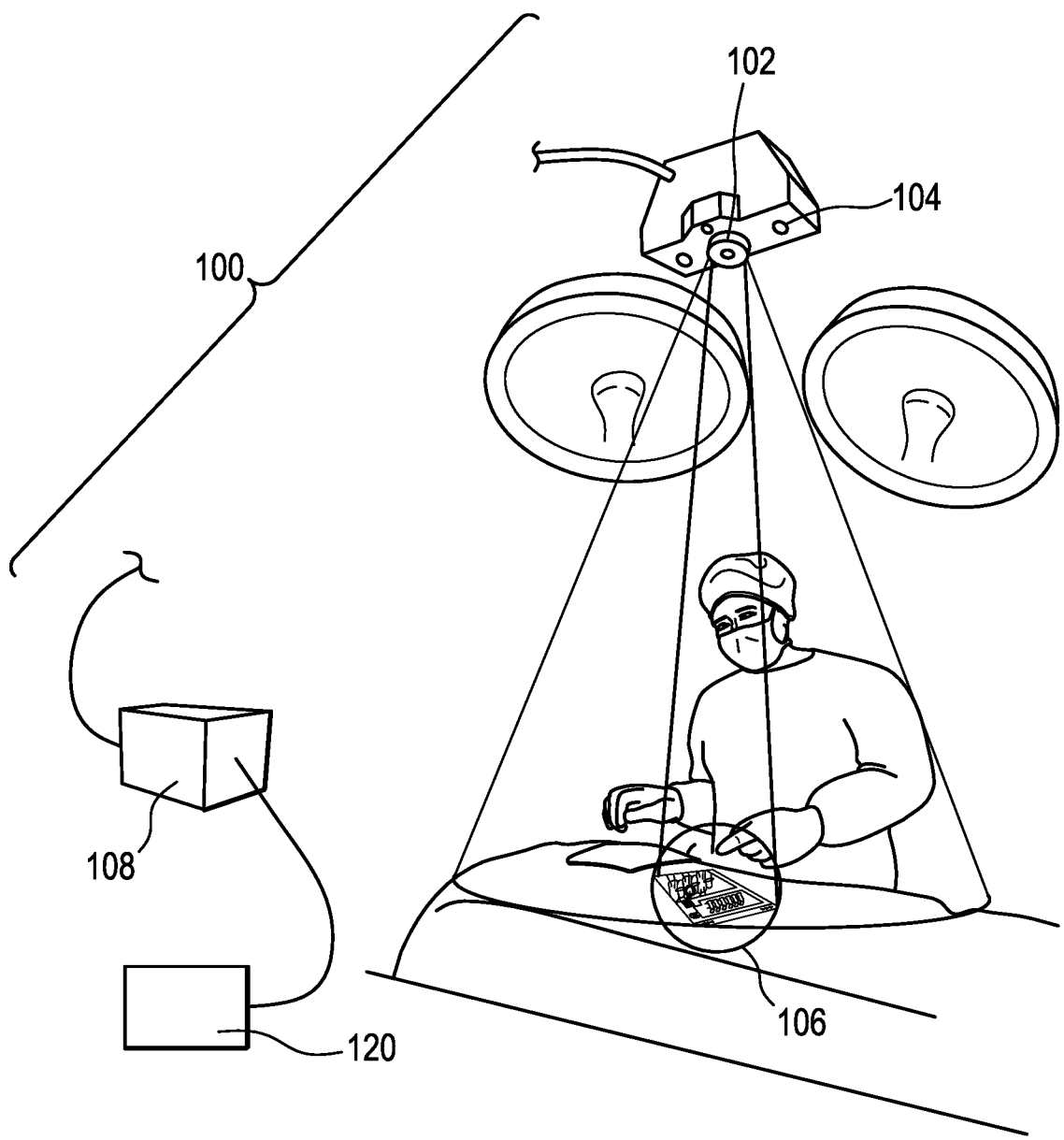
FIG. 1 is a schematic view of a user interface system in use in an operating room.

FIG. 1 illustrates an exemplary user interface system 100. The system can include a projector 102, a camera or sensor 104, a data board or substrate 106, and a controller 108. In use, the camera 104 can capture images of a working environment (e.g., the sterile field of an operating room as shown). The controller 108 can detect the data board 106 within the captured images and can determine a position and orientation of the data board within the sterile field. The controller 108 can thereby track movement of the data board 106 within the sterile field. Informed by this position and orientation information, the controller 108 can control the projector 102 to project an image onto the data board 106. The projected image can move with the data board 106 as the data board is moved within the working environment. The controller 108 can also detect other objects within the captured image, such as a user or a portion thereof (e.g., hands, fingers, fingertips, etc. of the user), a surgical instrument, a surgical implant, a stylus or other instrument held by a user, and so forth. The controller 108 can determine from the detected object information whether and how a user is interacting with the interface projected onto the data board 106, how an instrument or implant is being moved relative to a patient, and so forth.

In some embodiments, only the data board 106 is disposed within the working environment. One or more of the projector 102, the camera 104, and the controller 108 can be isolated from the working environment. Such isolation can be procedural, physical, or otherwise. For example, such components can be procedurally isolated by being disposed within the operating room but designated as non-sterile or non-touch components, such that they are not within the sterile field. By way of further example, such components can be physically isolated from the working environment, for example by being positioned remotely from the working environment, by being disposed opposite a physical barrier from the working environment, etc.

The projector 102 can be operatively coupled to the controller 108 by an input port, through which the projector can receive image or video signals from the controller. The projector 102 can include a light source and a lens system for projecting an image onto the data board 106 based on the received image or video signals. The projector 102 can receive control signals from the controller 108 indicating a target location to which the projection should be directed. The projector 102 can thus be configured to shift the position and/or orientation of the projected image based, e.g., on movement of the data board 106 within the working environment. The projector 102 can have an adjustable lens system (e.g., focal length, lens angle, lens position), can be mounted on a gimbal, gantry, or other movable mounting system, or can be otherwise configured to facilitate aiming of the projected image onto the data board 106 as the data board moves within the working environment. The projector 102 can be configured to project an image that is much larger than the data board 106, and can be controlled to only activate pixels which correspond to the current location and/or orientation of the data board. In such arrangements, the projector 102 and/or the lens system can be fixed within the working environment but can still "aim" the projected image onto the data board 106.

The camera or sensor 104 can be configured to detect various attributes of the working environment. For example, the camera or sensor 104 can be configured to detect the position and/or orientation of the data board 106. As another example, the camera or sensor 104 can be configured to detect the position and/or orientation of a user or a portion thereof (e.g., hands, fingers, fingertips, etc. of the user), a surgical instrument, a surgical implant, a stylus or other instrument held by a user, and so forth. The camera 104 can capture images of the working environment, which can be communicated to the controller 108 for processing to recognize the data board 106, user, or other objects within the captured images and to determine based on such information how such objects are moving or positioned within the working environment. Any of a variety of cameras or camera systems can be used, including RGB cameras, RGB-D cameras, infrared cameras, stereo cameras, and so forth. Exemplary RGB-D cameras include the Microsoft Kinect camera and the Microsoft Kinect V2 camera. The camera or sensor 104 can use structured light, time-of-flight, or other approaches known in the art to determine the distance between the camera and each pixel or region of the captured image. This information can be combined by the controller 108 with recognized object information to determine the distance between the camera 104 and the data board 106, between the camera and a user, etc.

The data board or substrate 106 can take various forms and can be configured to reflect light projected thereon by the projector 102. The data board 106 can be an inexpensive, single-use disposable. The data board 106 can be flexible. The data board 106 can be formed from paper, plastic, cardboard, metal, or combinations thereof. The data board 106 can be capable of efficient and non-destructive sterilization, e.g., via steam bath, radiation, and other known techniques. The data board 106 can be free of electronics in some embodiments, while in other embodiments electronic components can be utilized (e.g., ranging from more simple displays such as e-paper displays to liquid crystal displays and tablet computers).

The data board 106 can be partially or completely transparent. In some embodiments, the data board 106 can include an e-paper or liquid crystal display that can, among other things, allow users to have dynamic control over transparency of the data board 106. This can allow use cases in which the data board 106 is positioned over an item of interest in the working environment (e.g., a patient, surgical instrument, or the like) and images projected onto the data board provide an augmented reality or heads-up display effect without significantly obscuring the item of interest.

Once the data board 106 is overlaid over the item of interest, the data board 106 can allow active pass-through viewing of the data board 106 to observe the item of interest through one or more transparent sections of the data board 106. In some embodiments, the data board 106 can outline body structures such as nerves, organs, and/or other items of interest such that when the data board is placed over the body structures, the board can display an outline of the body structures while maintaining at least partial transparency so as not to obscure a view of the item of interest.

The data board 106 can be coated with holographic film or can include various other surface coatings or treatments to facilitate light reflection and improved display of the projected image. The data board 106 can be freely movable within the working environment. The data board 106 can be rested on a patient or other surface in the working environment, or can be mounted on a movable support arm, e.g., an arm of a surgical robot.

While a dedicated data board 106 is shown, in other arrangements the user interface can be projected onto other substrates, such as the patient (e.g., the patient's skin or surgically-exposed anatomical elements), a surgical drape covering the patient, an instrument (e.g., held by the surgeon), a glove or gloves worn by the surgeon or other user, a sterile dressing, a blue wrap, an implant, an operating table, a whiteboard, or any other surface within the working environment.

Figure 2:
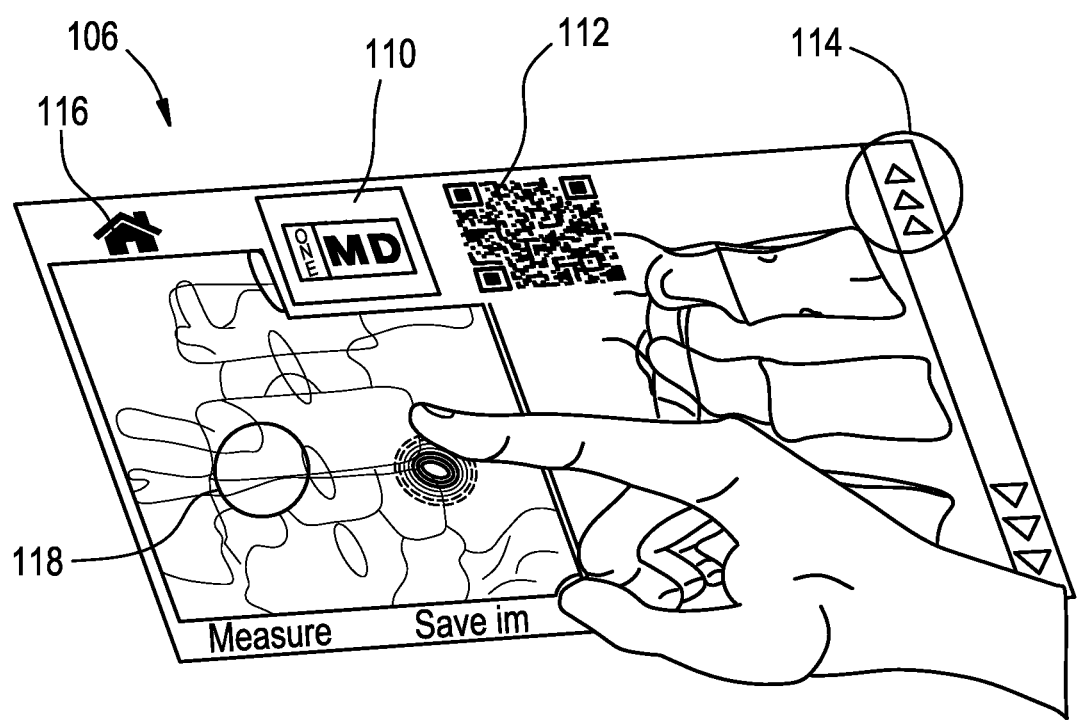
FIG. 2 is a perspective view of an exemplary data board of the user interface system of FIG. 1 and a user interacting with the data board.

FIG. 2 illustrates an exemplary data board 106 that can be used in the system 100.

The data board 106 can include a position marker 110. The position marker 110 can be a symbol or image having a known size, shape, or other characteristics to facilitate recognition of the position marker in captured images of the data board 106. While a single position marker 110 is shown, the data board 106 can include multiple markers, e.g., one at each end. Use of multiple markers 110 can improve tracking accuracy, field of view, or redundancy.

It will be appreciated that the structure and operation of the position marker 110 can vary depending on the type of navigation system used. In some embodiments, the position marker 110 can include one or more sphere-shaped or other fiducials for use with an optical navigation system, for example, a robotic navigation system. The fiducials can be arranged in predetermined positions and orientations with respect to one another. The fiducials can be aligned so as to lie in planes that are perpendicular to one another to set a Cartesian reference frame. The fiducials can be positioned within a field of view of a navigation system and can be identified in images captured by the navigation system. Exemplary fiducials include infrared reflectors, LEDs, spherical reflective markers, blinking LEDs, augmented reality markers, and so forth. The position marker 110 can be or can include an inertial measurement unit (IMU), an accelerometer, a gyroscope, a magnetometer, other sensors, or combinations thereof. The sensors can transmit position and/or orientation information to a navigation system, e.g., to a processing unit of the navigation system.

The position marker 110 can be detected by a navigation system, can communicate with a navigation system, or can be otherwise operably coupled to a navigation system to allow the position and/or orientation of the data board 106 and the underlying anatomy to be registered with and tracked by the navigation system. The position marker 110 can have a known location on the data board 106, e.g., known relative to the overall dimensions or boundaries of the data board. The position marker 110 can be asymmetrical, such that an orientation of the position marker relative to the camera 104 can be determined from a captured image of the position marker. The position marker 110 can be adhered to the data board 106, printed on the data board, or otherwise affixed or applied to the data board. In some embodiments, the shape of the data board 106 itself can serve as a position marker 110 to indicate a position of the data board. The position marker 110 can be used, as described below, to determine the position and/or orientation of the data board 106 or to track the data board within the working environment and/or with respect to the camera 102.

The data board 106 can include a unique identifier 112. The unique identifier 112 can be a QR code, bar code, serial number, ID number, or other marking or tag that uniquely identifies a particular data board or a particular group of data boards. The unique identifier 112 can be an RFID tag readable by the controller 108. The controller 108 can recognize the unique identifier 112 in captured images of the data board 106 and determine from said unique identifier information related to a task being performed in the working environment. For example, the unique identifier 112 can serve as a lookup key which can be used by the controller 108 to retrieve information from a database, such as a network connected server, cloud storage, and the like. Exemplary information that can be retrieved by the controller 108 based on the unique identifier 112 can include patient name, patient age, patient sex, patient date of birth, patient ID, patient images (e.g., pre-operative scans, CT, MR, X-ray, or PET images), PACS images, pre-operative plans, surgical inventory lists, surgical checklists or technique guides, and so forth. The unique identifier 112 can also be used to determine whether the data board 106 has been used previously, in which case the controller 108 may be configured to deny use of the data board, thereby enforcing a single-use policy.

The data board 106 can include static or non-projected interface elements 114. For example, the illustrated data board 106 includes a static up/down scroll bar 114. Exemplary static interface elements 114 can include scroll bars, buttons, keyboards, trackpads, sliders, radio buttons, text boxes, check boxes, icons, and the like.

The data board 106 can include projected interface elements 116. For example, the illustrated data board 106 includes an image of a "home" button 116 projected onto the data board by the projector 102. Exemplary projected interface elements 116 can include scroll bars, buttons, keyboards, trackpads, sliders, radio buttons, text boxes, check boxes, icons, and the like.

The data board 106 can include other projected content 118, such as patient X-ray images as shown.

The data board 106 can have any of a variety of shapes or contours. The data board 106 can have a concavity or convexity. The concavity or convexity can relate to projector location, e.g., to enhance the projected image.

The controller 108 can be operatively coupled to the camera 104 and the projector 102. The controller 108 can detect the data board 106 within images captured by the camera 104 and can determine a position and orientation of the data board within the working environment. The controller 108 can thereby track movement of the data board 106 within the working environment. Informed by this position and orientation information, the controller 108 can control the projector 102 to project an image onto the data board. The projected image can move with the data board 106 as the data board is moved within the working environment. The controller 108 can also detect other objects within the captured image, such as a user or a portion thereof (e.g., hands, fingers, fingertips, etc. of the user), a surgical instrument, a surgical implant, a stylus or other instrument held by a user, and so forth. The controller 108 can determine from the detected object information whether and how a user is interacting with the interface projected onto the data board 106, how an instrument or implant is being moved relative to a patient, and so forth. The controller 108 can include a back end that is operatively coupled to one or more pieces of controlled equipment 120, such that the controller can interact with the equipment based on a user's interaction with the data board 106. Exemplary controlled equipment 120 with which the controller 108 can interact can include surgical navigation systems, PACS (picture archiving and communication systems), cameras, electrosurgical generators, infusion pumps, vacuum valves, music players, and the like. The controlled equipment 120 can be disposed outside of the working environment (e.g., can be procedurally or physically isolated from the working environment). The controlled equipment 120 can alternatively be disposed within the working environment, or the controlled equipment can include equipment that is disposed within the working environment and equipment that is disposed outside of the working environment.

Figure 3:
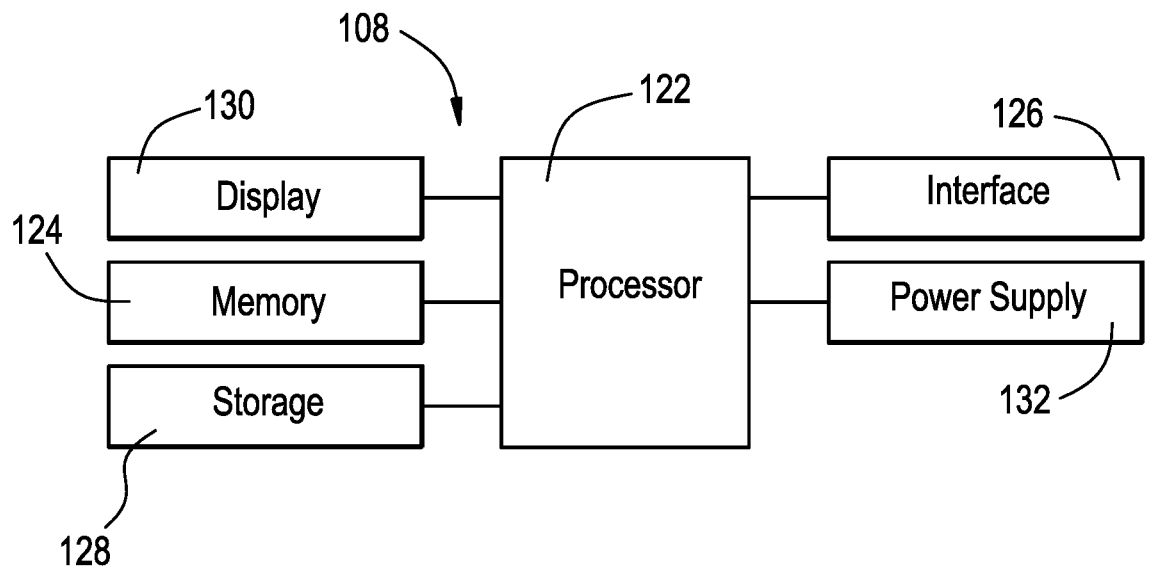
FIG. 3 is a schematic hardware diagram of a controller of the user interface system of FIG. 1.

FIG. 3 illustrates a block diagram of the physical components of an exemplary embodiment of the controller 108. Although an exemplary controller 108 is depicted and described herein, it will be appreciated that this is for sake of generality and convenience. In other embodiments, the controller 108 may differ in architecture and operation from that shown and described here. The controller 108 can be a tablet computer, mobile device, smart phone, laptop computer, desktop computer, cloud-based computer, server computer, multiple of the above, and so forth.

The illustrated controller 108 can include a processor 122 which controls the operation of the controller, for example by executing embedded software, operating systems, device drivers, application programs, and so forth. The processor 122 can include any type of microprocessor or central processing unit (CPU), including programmable general-purpose or special-purpose processors and/or any of a variety of proprietary or commercially-available single or multi-processor systems. As used herein, the term processor can refer to microprocessors, microcontrollers, ASICs, FPGAs, PICs, processors that read and interpret program instructions from internal or external memory or registers, and so forth. The controller 108 can include a memory 124, which can provide temporary or permanent storage for code to be executed by the processor 122 or for data that is processed by the processor. The memory 124 can include read-only memory (ROM), flash memory, one or more varieties of random access memory (RAM), and/or a combination of memory technologies. The various components of the controller 108 can be interconnected via any one or more separate traces, physical busses, communication lines, etc.

The controller 108 can include an interface 126, such as a communication interface or an I/O interface. A communication interface can enable the controller 108 to communicate with remote devices (e.g., other controllers or computer systems) over a network or communications bus (e.g., a universal serial bus). An I/O interface can facilitate communication between one or more input devices, one or more output devices, and the various other components of the controller 108. Exemplary input devices include the camera 104, the projector 102, touch screens, mechanical buttons, keyboards, and pointing devices. Exemplary output devices include the camera 104, the projector 102, electronic display screens, and speakers. The controller 108 can include a storage device 128, which can include any conventional medium for storing data in a non-volatile and/or non-transient manner. The storage device 128 can thus hold data and/or instructions in a persistent state (i.e., the value is retained despite interruption of power to the controller 108). The storage device 128 can include one or more hard disk drives, flash drives, USB drives, optical drives, various media disks or cards, and/or any combination thereof and can be directly connected to the other components of the controller 108 or remotely connected thereto, such as through the communication interface. The controller 108 can include a display 130, and can generate images to be displayed thereon. In some embodiments, the display 130 can be a vacuum fluorescent display (VFD), an organic light-emitting diode (OLED) display, or a liquid crystal display (LCD). The controller 108 can include a power supply 132 and appropriate regulating and conditioning circuitry. Exemplary power supplies include batteries, such as polymer lithium ion batteries, or adapters for coupling the controller 108 to a DC or AC power source (e.g., a USB adapter or a wall adapter).

The various functions performed by the controller 108 can be logically described as being performed by one or more modules. It will be appreciated that such modules can be implemented in hardware, software, or a combination thereof. It will further be appreciated that, when implemented in software, modules can be part of a single program or one or more separate programs, and can be implemented in a variety of contexts (e.g., as part of an embedded software package, an operating system, a device driver, a standalone application, and/or combinations thereof). In addition, software embodying one or more modules can be stored as an executable program on one or more non-transitory computer-readable storage mediums. Functions disclosed herein as being performed by a particular module can also be performed by any other module or combination of modules, and the controller can include fewer or more modules than what is shown and described herein. One or more modules can be implemented by the camera 104, by the projector 102, by another device, or by combinations thereof.

Figure 4:
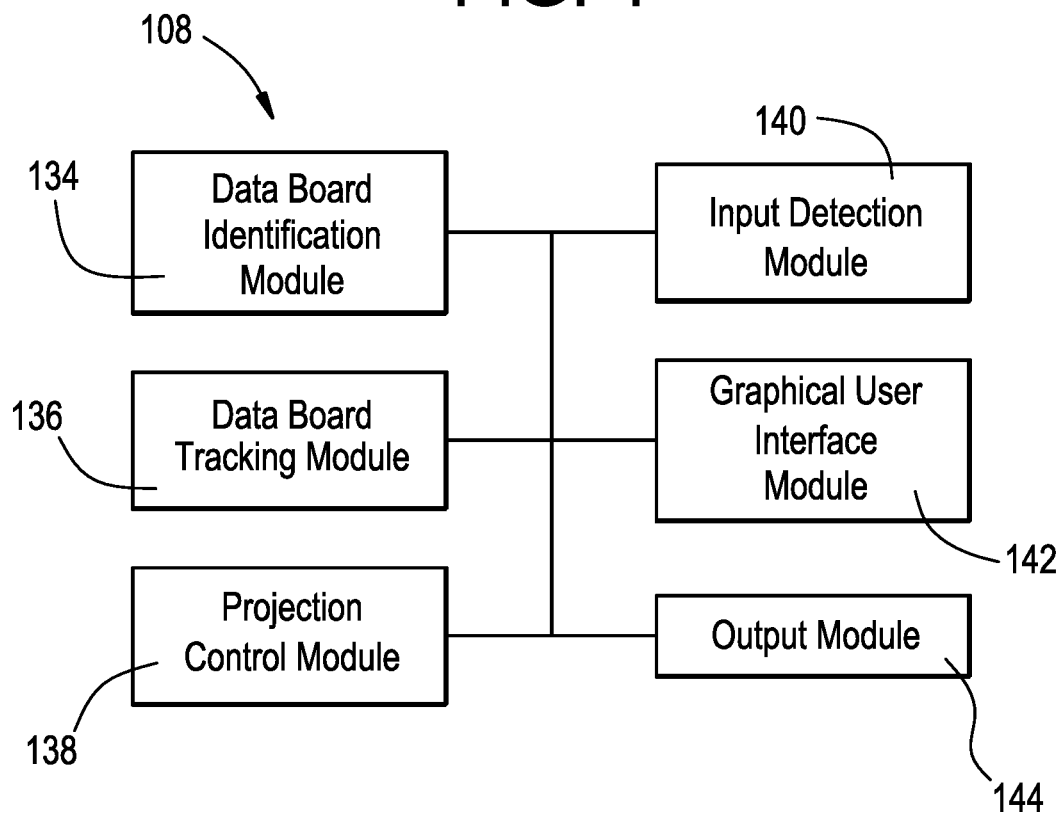
FIG. 4 is a functional block diagram of the controller of FIG. 3.

FIG. 4 is a schematic diagram of the modules of one exemplary embodiment of the controller 108.

The controller 108 can include a data board identification module 134. The data board identification module 134 can receive one or more captured images of the data board 106 and can recognize the unique identifier 112 of the data board within said images. Alternatively, or in addition, the data board identification module 134 can receive the unique identifier from an RFID reader or other device coupled to the controller 108. Once determined, the unique identifier can be used by the controller 108 to retrieve various information about the data board 106, the working environment, or objects within the working environment, as described above.

The controller 108 can include a data board tracking module 136. The data board tracking module 136 can determine the position and/or orientation of the data board 106 relative to a reference, e.g., a coordinate system of the camera 104 or a coordinate system of the working environment. The data board tracking module 136 can determine changes in said position and/or said orientation.

The data board tracking module 136 can receive images of the working environment captured by the camera 104. The data board tracking module 136 can detect the data board 106 or a portion thereof, e.g., the position marker 110, within the captured images. In a typical arrangement in which the camera 104 is positioned above the working environment in a bird's eye view, positioning of the data board 106 along X and Y axes of the working environment can be determined by the location of the data board within the overall captured image. Positioning of the data board 106 along a Z axis of the working environment can be determined based on the distance between the data board and the camera 104. The captured images can include explicit distance information, e.g., in the case of images captured by a RGB-D camera. In embodiments in which the camera image data does not necessarily include explicit distance information, the depth can be calculated or inferred by determining the size of the position marker 110 or data board 106 within the image, the size or angle of the position marker's or data board's edges or other features, and so forth.

Pitch and yaw of the data board 106 (e.g., rotation about the X and Y axes) can be determined by comparing distance-to-camera information for multiple points of the data board image. A difference in distance-to-camera between one region and another region of the position marker or the data board image can indicate that the data board 106 is tilted towards or away from the camera and the direction of the tilt. Roll of the data board 106 (e.g., rotation about the Z axis) can be determined by comparing the 2D orientation of the position marker 110 or data board 106 in the captured image to a predetermined 2D orientation of the position marker on the physical data board.

The data board tracking module 136 can compare multiple camera images captured over time to determine and track changes in any of the above parameters, i.e., changes in the position and/or orientation of the data board 106.

The data board tracking module 136 can thus track the position and/or orientation of the data board 106, e.g., in real time or substantially in real time.

The controller 108 can include a projection control module 138. The projection control module 138 can send image data to the projector 102 to be projected onto the data board 106. The image data can be adjusted by the controller 108 based on the determined position and/or orientation of the data board 106. Alternatively, or in addition, the projection control module 138 can send control signals to the projector 102 to control the location and/or orientation of the projected image, e.g., to direct the projected image onto the data board 106, to project the image onto the data board only, and/or to compensate the projected image for any tilt or rotation of the data board relative to the projector.

For example, when the data board tracking module 136 determines that the data board 106 has shifted in the X or Y direction, the projected image can be shifted to a corresponding degree in the X or Y direction. As another example, when the data board tracking module 136 determines that the data board 106 has shifted in the Z direction, the projected image can be scaled accordingly to match the movement of the data board. As another example, when the data board tracking module 136 determines that the data board 106 has rotated about the Z axis, the projected image can be rotated accordingly. As yet another example, when the data board tracking module 136 determines that the data board 106 has tilted, a keystone correction algorithm can be applied to the image data such that the projected image maps accurately to the tilted data board without distortion.

The projection control module 138 can thus maintain an accurate projected image on the data board 106 as the data board moves in one or more degrees of freedom within the working environment. The projected image can follow the data board's movement in real time or substantially real time.

The controller 108 can include an input detection module 140. The input detection module 140 can determine from image data captured by the camera 104 whether and how a user is interacting with the data board 106. For example, the input detection module 140 can use various known image processing routines to identify a user or a portion of a user in images captured by the camera 104. Exemplary image processing routines include edge detection, blob detection, and the like. In some embodiments, the user can wear a glove having a predetermined color or pattern to facilitate identification of the user's finger in captured images. In the case of images with explicit distance-to-camera information, the input detection module 140 can calculate the difference in distance-to-camera between the user's finger and the data board 106. If the difference in distance-to-camera is below a threshold amount, the input detection module 140 can determine that the user's finger is contacting the data board 106. In the case of images that do not necessarily include explicit distance-to-camera information, the input detection module 140 can look for Z-direction movement of the user's finger when the finger is superimposed over the data board 106 to determine that the user is tapping on the data board. Changes in X or Y positioning of the user's finger while the user's finger is determined to be in contact with the data board 106 can be interpreted by the input detection module 140 as swipe, pinch, drag, or other input gestures. While use of hand gestures to interact with the system are generally described above, it will be appreciated that the user can alternatively or in addition interact with the system using a stylus or other instrument. For example, the user can interact with the system using any instrument that they happen to be holding at the time. In the case of a dedicated stylus or other instrument for interacting with the system, the stylus or instrument can be disposable or reusable, and can include electronics or can include no electronics.

In some embodiments, the data board 106 can be controlled based on a perspective and/or location of a user, e.g., virtual reality tracking. The user can interact with the data board 106 using eye movement or changes in head position and/or orientation to control a dynamic viewer perspective. For example, a position marker 110 can be secured, placed, or otherwise affixed at a location that is on, or relative to, the head of a user. Movement, tilt, or other changes in position of the head can change the perspective that the user sees. In some embodiments, changes in head position can control a clipping plane perspective, as discussed further below, so as to change the perspective of a two-dimensional rendering on a screen to appear in three dimensions. Knowing a position of the patient, the data board 106, and the user's head position, a rendered perspective view can allow the user to see a three-dimensional perspective view of an object of interest, e.g., a patient's anatomy. In some embodiments, a position marker 110 can be placed on glasses, contact lenses, and so forth to track and/or control a perspective to account for eye movement. In other embodiments, one or more cameras can be used to monitor and track movement of a user's eyes. For example, any of an RGB and an infrared camera can be utilized to monitor the position of a user's eyes and direction of their gaze. It will be appreciated that changes of dynamic viewer perspective can be tracked for multiple users by placing position markers on multiple users to track head position and eye movement. In some embodiments, each such tracked user can have their own data board 106 with an image projected thereon that provides a unique perspective based on their tracked head position, gaze direction, etc.

The controller 108 can include a graphical user interface module 142. The graphical user interface module 142 can generate image data representing a graphical user interface. The image data can be communicated to the projection control module 138 to be projected onto the data board 106. User inputs detected by the input detection module 140 can be communicated to the graphical user interface module 142, which can apply those inputs to the user interface and update the user interface accordingly. For example, upon detection of a user's click or tap gesture over a button projected onto the data board 106, the graphical user interface module 142 can execute an event handler associated with the button click, e.g., to display a dialog box associated with the button or to control equipment 120 associated with the button. The graphical user interface module 142 can present user interface controls for projection onto the data board 106, said controls corresponding to the controls of equipment 120 to which the controller 108 is operatively coupled.

When a user interacts with projected controls, the graphical user interface module 142 can instruct an output module 144 to interact with a piece of controlled equipment 120. For example, the output module 144 can generate a control signal to apply an interaction to equipment 120 operatively coupled to the controller 108. For example, the voltage on a signal line can be toggled to effect a setting change on a piece of digital equipment 120 to which the controller 108 is coupled, such as a navigation system, PACS, etc.

Moreover, the information displayed on the data board 106 can be dynamically updated based on user interaction with the data board 106 (e.g., via menus, etc.) and/or physical interaction with other equipment, to allow a user to control the equipment through the graphical user interface projected on the data board. For example, the data board 106 could be utilized during a setup or calibration procedure for three-dimensional navigation by showing navigation settings on the data board 106 for any instrument that a user touches directly or selects in the graphical user interface. Such techniques can apply to instrument operating parameters as well. For example, when a user touches a particular instrument or portion thereof directly or in the graphical user interface (via, e.g., a menu selection or direct selection on a projected image of the instrument), various settings for the instrument can be projected on the data board 106 to allow the user to view and/or adjust such settings. For example, a user might touch a distal portion of a burr tool directly or touch the burr of an image of the tool projected on the data board 106 to be presented with adjustable settings for burr speed, etc. The ability to dynamically display relevant data and provide a user control interface on the data board 106 (or wherever the interface is projected, e.g., surgical drape on patient, etc.) can be applied to any instrument utilized in a procedure. This can allow the user to access and adjust settings for any instrument inside the sterile field.

FIG. 5 illustrates an exemplary method of using the system 100. In step S1, one or more images of a working environment can be captured, e.g., using the camera 104. In step S2, the captured images can be used to determine a position and/or an orientation of a substrate, e.g., the data board 106. The position and/or orientation can be determined relative to the camera 104, relative to the working environment, or relative to some other reference frame. In step S3, a projected image can be projected onto the substrate. For example, the projector 102 can be used to project a graphical user interface onto a data board 106. The projected image can be moved, scaled, angled, or otherwise adjusted in coordination with the determined position and/or orientation of the substrate. In step S4, user interaction with the substrate can be determined. For example, the controller 108 can process captured images to determine whether the user is interacting with the substrate 106, e.g., by applying a touch, tap, swipe, slide, drag, pinch, or other input gesture. In step S5, equipment can be controlled based on user interaction detected in step S4. For example, the controller 108 can control equipment 120 disposed outside of the working environment based on user interaction with the projected graphical user interface. In some embodiments, the controller 108 can display errors or warning messages associated with the equipment 120 by projecting such information onto the graphical user interface. In other embodiments, information such as errors or warnings can be conveyed to a user by projecting patterns or other indicators around the surgical site to ensure notification. Such notifications can be accompanied by, e.g., more detailed information conveyed through the graphical user interface projected onto the data board 106.

The system 100 can be used in a surgical setting. For example, the data board can be positioned within the sterile field in proximity to a patient and a surgeon. The surgeon can interact with a graphical user interface projected onto the data board. The surgeon can scroll or click through different tabs associated with different pieces of controlled equipment. Each tab can include graphical user interface controls for adjusting or interacting with said equipment.

The data board can include a QR code linked to a patient data or PACS system. When a fluoro shot or other patient image is captured, it can be linked with the patient data by a patient ID entered into the C-arm or imaging device, and it can be automatically displayed on the data board for reference by the surgeon. The surgeon can interact with the data board to take simple anatomical measurements, such as angular corrections in spinal surgery. The surgeon can interact with the data board to manipulate a 3-D data set representation of the patient anatomy. The camera 104 can be used to recognize unique implants within the surgical site and the system can link or associate those implants to a patient ID, e.g., in a patient database.

While a data board is described above, the system 100 can also project information onto other surfaces or objects. For example, information can be projected onto an observation source (not shown), such as a surgical microscope, glasses, loupes, and so forth that are worn or used by the user. The unique identifier 112 can be attached to a patient drape or another location relative to the patient such that patient position and/or orientation relative to the system 100 can be defined. The input detection module 140 can identify a user or a portion of a user in images captured by the camera 104 to determine a position of the user's hands or surgical tools being used during the procedure, as well as the position of the patient and other components, e.g., a data board or drape that may have information projected thereon. The system 100 can determine the relative position and/or orientation of the patient with respect to these other components and the graphical user interface module 142 can project images or other data onto the observation source instead of, or in addition to, a substrate such as the data board 106, to synchronize the image with the anatomy of the patient. It will be appreciated that the projected image can be superimposed on top of a patient and, in some embodiments, the projected image can be transparent such that the patient can be seen through the observation source. Further, the projected image can be displayed within the user's field of view without being directly in front of the user or overlaid on the patient. In some embodiments, information, such as warnings, error messages, etc., can be projected throughout the surgical site via patterns, as well as other alerts, sounds, flashing lights, etc., to ensure that users are sufficiently notified. These warnings can also be projected onto the data board 106 in greater detail to notify users of the nature of the error, warning, etc.

In some embodiments, the system 100 can receive inputs from a surgical navigation system and can project navigation feedback onto an instrument being used by the surgeon. For example, the system can project a first indicator, e.g., a green circle, onto the instrument when the instrument is aligned with a predetermined target trajectory. The system can project a second indicator, e.g., a red letter 'X', onto the instrument when the instrument deviates from the predetermined target trajectory. The system can project an indicator, e.g., an arrow or triangle, onto the instrument to indicate the current tip direction or orientation of the instrument. The above-described indicators can be projected onto a handle of the instrument, a shaft of the instrument, or any other portion of the instrument. While a separate surgical navigation system is described above, the system 100 can also include an integrated navigation system, or can receive inputs from other patient reference sources.

In some embodiments, the system 100 can be used to execute a procedure that was pre-planned. For example, in the surgical setting, the system 100 can be connected to a pre-operative planning software, e.g., Surgimap, while outside of the working environment to map out a plan of the procedure to be performed. The plan can then be projected onto the substrate 106 in the working environment to perform the procedure. Some non-limiting examples of system uses can include setting a predetermined trajectory of surgical tools, correction of trajectory of surgical tools, tabulation of surgical tools used, and so forth. In some embodiments, the plan can include a checklist that the system 100 can project onto the substrate 106 to allow the user to check off and advance through the items of the checklist using the touch and/or hand gestures discussed above.

The system 100 can project the output of a surgical camera, such as an endoscope or a miniaturized camera disposed in a working channel of a surgical access device, onto the data board. The data board 106 can also show a navigation screen for the camera to inform the user about the location of the camera relative to the working channel. The system 100 can augment the displayed camera feed, as well as the feed derived from integrated equipment, for example by projecting a colored highlighting or other indicator over nerves or other delicate structures detected in the camera feed or by projecting a measurement scale over the camera feed. In some embodiments, the data board 106 can display EKG or ECG and/or other neuro-monitoring measurements taken by the system, along with anything else that can be similarly displayed on a tablet computer or other display. It will be appreciated that the system 100 can use position and/or orientation information of the data board 106 and the patient to ensure that the image is adjusted such that a virtual anatomy of the patient aligns with the physical anatomy of the patient.

Figure 6A:
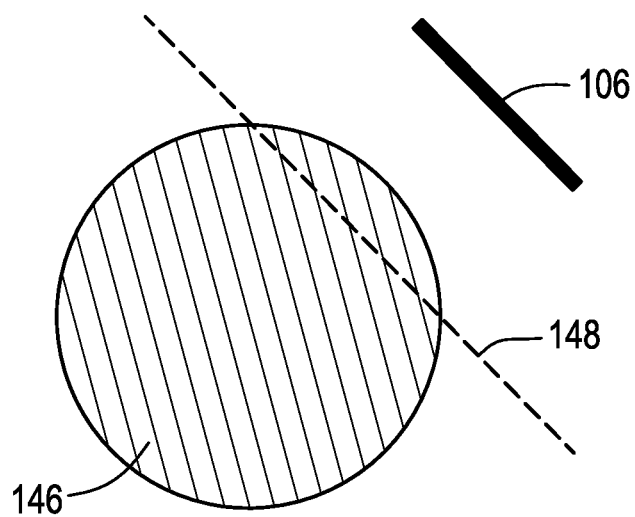
FIG. 6A illustrates a data board and an associated plane of visualization with respect to a patient.
Figure 6B:
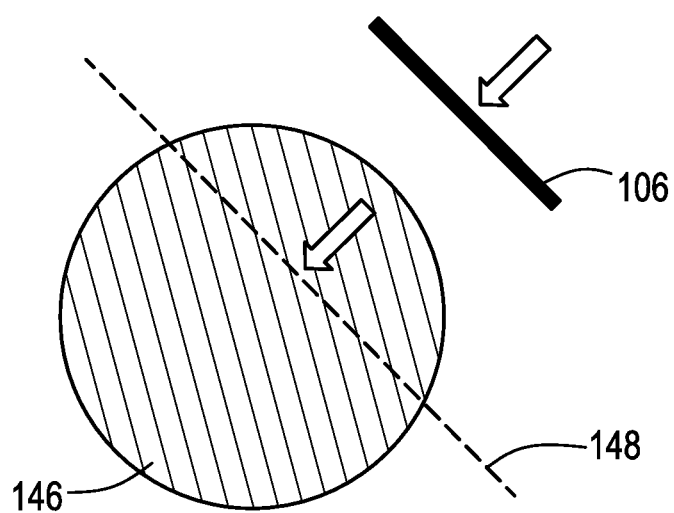
FIG. 6B illustrates adjusting a position of the data board of FIG. 6A relative to the patient to adjust a position of the plane of visualization relative to the patient.
Figure 6C:
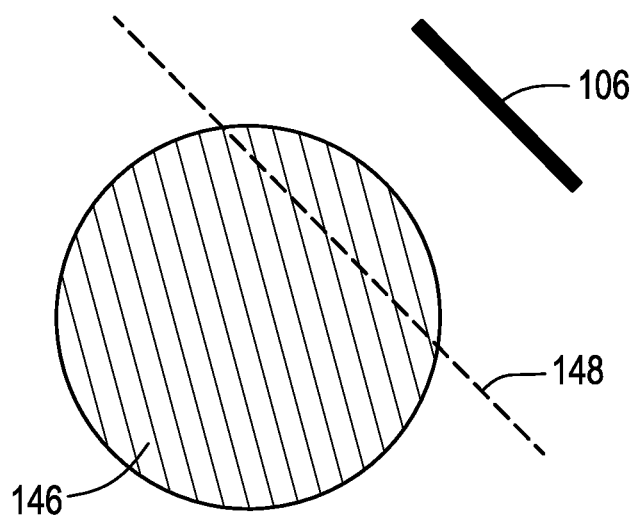
FIG. 6C illustrates a data board and an associated plane of visualization with respect to a patient.
Figure 6D:
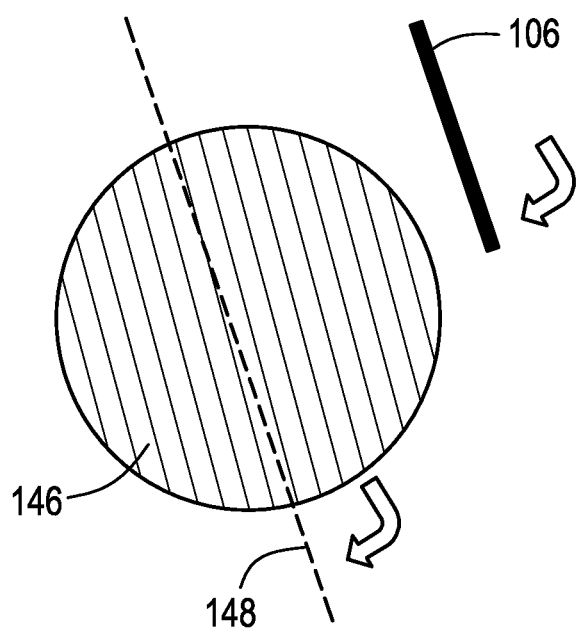
FIG. 6D illustrates adjusting an orientation of the data board of FIG. 6C relative to the patient to adjust an orientation of the plane of visualization relative to the patient.

Physical movement of the data board by the user can be interpreted as a user input gesture. For example, the data board can work like a clipping plane, with movement of the data board sectioning 3-D data displayed on the data board in accordance with said movement. FIGS. 6A-6D illustrate an example in which a data board 106 is moved relative to a patient 146 to change a plane of visualization 148 displayed on the data board (e.g., a plane of visualization within a 3-D data model of the patient). As shown in FIGS. 6A and 6B, adjusting the position of the data board 106 relative to the patient 146 can be effective to adjust the position of the plane of visualization 148 by a proportional or equal amount. For example, as indicated by the arrows, moving the data board 106 towards the patient 146 can cause the plane of visualization 148 to move deeper into the patient). Similarly, as shown in FIGS. 6C and 6D, adjusting the orientation of the data board 106 relative to the patient 146 can be effective to adjust the orientation of the plane of visualization 148 by a proportional or equal amount. For example, as indicated by the arrows, tilting one side of the data board 106 towards the patient 146 can cause the plane of visualization 148 to also tilt.

In applications where a tablet computer may be used, the data board can provide a complete replacement for the tablet computer, eliminating the need to place electronics or sensitive components within the working environment. In embodiments that include a tablet computer, the tablet computer can be bagged or wrapped in a sterile drape or cover to be used in the working environment. A user can interact with the tablet in the working environment to perform surgical tasks in a manner similar to how the user can interact with a passive data board, as described above. The system can track the tablet computer in order to change the perspective of displayed patient anatomy, track surgical tools, and so forth. Upon completion of the procedure, the tablet computer can be removed from the working environment, sterilized, and reused, if necessary.

In embodiments that utilize a passive data board, the system 100 can provide an interactive touch screen user interface in a working environment without necessarily having to place any electronics in the working environment.

The system 100 can provide a single user interface for interacting with many disparate systems that may be used in connection with a workflow performed in the working environment. In the case of a surgical operating room, a user can interact with many different systems within the sterile field or outside the sterile field, all through the data board. The data board can be used to display pre-operative films, make measurements on a PACS, adjust settings of devices outside of the sterile field, interact with surgical navigation systems and the user interfaces thereof, position display of digital information in direct proximity to a patient or within surgeon line of sight, and so forth.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. A user interface system, comprising:
a projector configured to receive control signals from a controller indicating a target location to which a projection should be directed;
a data board having the target location designated thereon;
a sensor configured to capture images of the working environment containing the data board: and
a controller operatively coupled to the sensor and the projector, the controller comprising:
a data board tracking module configured to detect the data board within images captured by the sensor and determine a position and orientation of the data board within the working environment substantially in real-time; and
a projection control module that is configured to send image data to the projector for projection onto the data board;
wherein the controller is configured to control the projector to aim the projection onto the data board based on the position and orientation of the data board;
wherein the data board is configured to be moved an amount in one or more directions to adjust a position of a plane of visualization displayed on the data board to section three-dimensional data projected on the data board proportionally to the amount of movement; and
wherein the projector is configured to project over an area that is larger than the data board, the projector being capable of activating only a selected portion of available pixels which correspond to a current location or orientation of the data board to aim the projection onto the data board.

2. The system of claim 1, wherein the controller is configured to track movement of the data board within the working environment such that the projection moves with the data board as the data board is moved within the working environment.

3. The system of claim 1, further comprising a surgical access device having an imaging component disposed in a working channel thereof, the surgical access device being configured to interact with the controller to project the output of the imaging component onto the data board.

4. The system of claim 3, wherein the imaging component includes one or more of a surgical camera, an endoscope, or a miniaturized camera configured to pass through the working channel.

5. The system of claim 1, wherein one or more of the projector, the sensor, and the controller is disposed outside of the working environment.

6. The system of claim 5, wherein one or more of the projector, the sensor, and the controller is positioned remotely from the working environment or disposed opposite a physical barrier from the working environment.

7. The system of claim 1, wherein the data board includes a display having an adjustable transparency such that the projection provides an augmented reality or heads-up display effect without significantly obscuring an item of interest beneath the data board.

8. The system of claim 7, wherein the display is configured to be adjusted to outline body structures such that when the data board is placed over the body structures, the data board displays an outline of the body structures while maintaining at least partial transparency so as not to obscure the item of interest.

9. The system of claim 1, wherein the data board includes one or more position markers associated therewith to determine the position or orientation of the data board.

10. The system for claim 9, wherein the data board further comprises static or non-projected interface elements on a surface thereof, the static interface elements including one or more of scroll bars, buttons, keyboards, trackpads, sliders, radio buttons, text boxes, check boxes, or icons.

11. The system of claim 1, wherein the controller is further configured to interact with controlled equipment based on the user's interaction with the data board, the controlled equipment including surgical navigation systems, picture archiving and communication systems, cameras, electrosurgical generators, infusion pumps, vacuum valves, or music players.

12. The system of claim 1, wherein, when the data board tracking module determines that the data board has shifted in a first direction, the projection is shifted to a corresponding degree in the first direction in substantially real-time.

13. The system of claim 1, wherein the controller further comprises an input detection module configured to determine from image data captured by the sensor how the user is interacting with the data board and to change the projection on the data board to correspond to the interaction.

14. The system of claim 1, wherein the data board is configured to be controlled based on a perspective or location of the user using eye movement or changes in head position or orientation to control a dynamic viewer perspective.

15. The system of claim 14, wherein movement, tilt, or changes in position of the head of the user controls a clipping plane perspective of the user such that a perspective of a two-dimensional rendering on the data board appears in three dimensions.

16. The system of claim 1, wherein the controller is configured to dynamically update the information displayed on the data board based on user interaction with the data board to allow the user to control the equipment through the graphical user interface projected on the data board.

* * * * *